United States Patent [19]

Arndt et al.

[11] 4,130,414
[45] Dec. 19, 1978

[54] 1,2,3-THIADIAZOLE-5-YL-UREA DERIVATIVES, PROCESS FOR MAKING THE SAME AND PLANT RETARDATION AND DEFOLIATION COMPOSITION CONTAINING SAME

[75] Inventors: Friedrich Arndt; Hans-Rüdolf Kruger; Reinhart Rusch, all of Berlin, Fed. Rep. of Germany

[73] Assignee: Schering AG, Berlin and Bergkamen, Fed. Rep. of Germany

[21] Appl. No.: 792,016

[22] Filed: Apr. 28, 1977

[30] Foreign Application Priority Data

May 3, 1976 [DE] Fed. Rep. of Germany ....... 2619861

[51] Int. Cl.² .................... A01N 9/22; C07D 417/12
[52] U.S. Cl. ...................................... 71/90; 544/331; 546/277
[58] Field of Search ............... 260/294.8 D, 295 E; 71/90

[56] References Cited

U.S. PATENT DOCUMENTS

| | | | |
|---|---|---|---|
| 3,293,257 | 12/1966 | Woods et al. | 260/295 E |
| 3,929,816 | 12/1975 | Rathgeb et al. | 260/306.8 D |
| 3,956,315 | 5/1976 | Kobzina | 260/332.2 A |

*Primary Examiner*—Alan L. Rotman
*Attorney, Agent, or Firm*—Michael J. Striker

[57] ABSTRACT

1,2,3-Thiadiazole-5-yl-urea derivatives of the formula

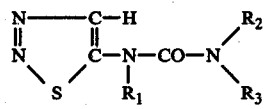

in which $R_1$ is hydrogen or alkyl of 1 to 5 carbon atoms, $R_2$ is hydrogen or alkyl from 1 to 5 carbon atoms which latter may also have at least one oxygen or sulfur atom interposed in the carbon chain and wherein $R_3$ is a heterocyclic hydrocarbon residue in which at least one nitrogen atom is present in the ring, which residue may also be substituted by the same or different substituents comprising alkyl of 1 to 4 carbon atoms, alkoxy of 1 to 4 carbon atoms, halogen, nitro or trifluoromethyl. The compounds are effective as agents for growth retardation and defoliation of plants.

The invention also comprises a process of making the product and compositions in which the products are the, or one of the, effective agents.

12 Claims, No Drawings

1,2,3-THIADIAZOLE-5-YL-UREA DERIVATIVES, PROCESS FOR MAKING THE SAME AND PLANT RETARDATION AND DEFOLIATION COMPOSITION CONTAINING SAME

BACKGROUND OF THE INVENTION

The invention relates to novel 1,2,3-thiadiazole-5-yl-urea derivatives and the process for making the same.

As growth retardation agent, maleic acid hydrazide has been widely used (German Pat. No. 815,192) which, however, has an unsatisfactory action in case of use of lower amounts. For the same purpose it has also been proposed to use substituted carbamoylamino-1,2,3-thiadiazoles, see German published application 2.214.632. However, it has been found that these latter agents cause damage in the form of burns to grasses.

Plant defoliation agents have also become known, among them particularly tri-n-butyl-trithiophosphate, U.S. Pat. No. 2,965,467. This compound, however, does not always have a satisfactory activity and in addition has an unpleasant odor which is resented by persons handling it.

It is therefore the object of the present invention to provide an agent which has a higher activity in plant growth retardation and defoliation than the mentioned compounds and is free from problems in handling it.

SUMMARY OF THE INVENTION

The compounds of the invention are 1,2,3-thiadiazole-5-yl-urea derivatives of the formula

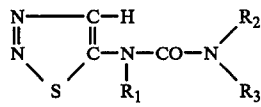

in which $R_1$ is hydrogen or alkyl of 1 to 5 carbon atoms, $R_2$ is hydrogen or alkyl of 1 to 5 carbon atoms which latter may also have at least one oxygen or sulfur atom interposed in the carbon chain and be substituted like $R_3$ $R_3$ is a heterocyclic hydrocarbon residue in which at least one nitrogen is present in the ring, which residue may also be substituted by the same or different substituents selected from the group consisting of alkyl of 1 to 4 carbon atoms, alkoxy of 1 to 4 carbon atoms, halogen, nitro and trifluoromethyl.

The compounds of the invention are preferably made by reacting a compound of the formula

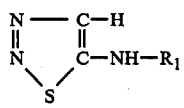

with a chloroformic acid ester of the formula $Cl-CO-X-R_4$ in the presence of an acid acceptor in an organic solvent at a temperature of 0° to 60° C., and then reacting the thus-obtained product with an amine of the formula

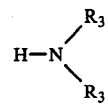

in an organic solvent at a temperature of 50° to 150° C. and recovering the desired urea derivative, $R_1$, $R_2$, and $R_3$ in these formulae having the meaning as above, X being oxygen or sulfur and $R_4$ being alkyl of 1 to 4 carbon atoms or being aryl.

The compounds of the invention delay in particular the vegetative growth which frequently is desirable in case of agricultural plants. With the compounds of the invention there can furthermore be obtained other desirable activities such as for instance the defoliation of plants, the increased formation of graft shoots, and a shortening of the axial members of the plant.

DISCUSSION OF THE INVENTION AND PREFERRED EMBODIMENTS

The compositions of the invention are preferably used for the purpose of regulating plant growth in an amount of 0.05 to 5 kg of effective agent per about 2.5 acres (specifically per 1 hectare). These limits in specific cases can also be exceeded both downwards and upwards.

The type and manner of the plant regulating action depends also on the time of application, on the type of plant and on the concentration.

The compounds of the invention can be applied in various manners to different plant parts such as to the seeds, the root, the stem, the leaves, the blossoms and the fruits. The compounds can also be applied by spraying in a preemergence or prebudding application or post-emergence or post-budding application. In case of a number of weeds the retardation can occur in a manner that is tantamount to a complete blockage of the development including plants such as brush.

Although it is possible to use lethal amounts of the compounds of the invention, it is contemplated to actually employ only those amounts which are necessary for obtaining the above-described action. The natural growth regulation effected by the compounds of the invention results in a morphological change in the plant which can easily be determined by visual observation. Similar changes can also be established in the size, the shape, and the color of the plants, and of any of their parts.

In general, the activity can be considered as retardation. It is believed that this is due to a change of the hormone supply of the plants.

With specific plants this retardation or blockage of the development results in a reduction or blockage of the tip growth the result of which is a shorter main stalk or stem and an increased branching. These changes of the natural growth result in smaller and more bushy plants.

Of these phenomena various uses can be made for accomplishing different ends.

For instance in case of many plants such as potatoes, sugar cane, sugar beets, grapes, melons, fruit trees, and silage plants, and reduction of the apical growth may result in an increase of the carbohydrate contents of the plants when harvested. In case of fruit and plantation plants the reduction of the plant growth results in shorter, more fully bodied branches which makes the individual branches more easily accessible and thus makes the harvesting easier. In case of grasses, a reduction of the vertical growth is sometimes desirable because the time intervals for mowing can thus be extended.

A specific effect of the use of the compounds of the invention is defoliation of the plants. It is known among experts that defoliation is no herbicidal action and that the killing off of the plant may even be undesirable since the leaves of the dead plant may remain in place and may cause damage to the productive portions of the plant. The idea of a defoliation to make the harvesting easier and to result in higher quality harvested products can thus be vitiated. It is therefore necessary to keep the plant alive while the leaves become separated and drop off. This permits the further development of the productive portions of the plant but should prevent the further propagation of the leaves.

All these problems are met in perfect manner by the compounds of the invention as distinguished from similar compounds of the prior art.

The compounds of the invention can either be used by themselves or intermixed with each other or mixed with other active agents. If desired, other defoliation, plant protection or pesticide agents may be added.

The activity and speed of action can for instance be increased by additives such as organic solvents, cross-linking agents and oils. This, on the other hand, may also permit a reduction of the amount to be used.

The compounds of the invention can in particular be improved in their activity by use together with compounds which also have growth regulating effects such as, for instance, auxin, α-(2-chlorophenoxy)-propionic acid, 4-chlorophenoxyacetic acid, 2,4-dichlorophenoxyacetic acid, indolyl-3-acetic acid, indolyl-3-butyric acid, α-naphthylacetic acid, β-naphthoxyacetic acid, naphthylacetamide, β-N-m-tolylphthalamic acid, gibberellines, abscisinic acid, tri-n-buty-trithiophosphate, cytoquinines, 2-chloroethylphosphonic acid, 2-chloro-9-hydroxyfluorene-9-carboxylic acid derivatives, 2-chloroethyl-trimethylammoniumchloride, N,N-dimethylaminosuccinic acid, 2-isopropyl-4-dimethylamino-5-methylphenyl-1-piperidine, phenyl-isopropylcarbamate, 3-chlorophenyl-isopropylcarbamate, ethyl-2-(3-chlorophenylcarbamoyloxy)propionate, maleic acid hydrazide, 2,3-dichlorisobutyric acid, O,O-dimethyl-dithio-thioformate, 1,1'-dimethyl-4,4-bipyridilium-dichloride, fatty acids, chlorates, nonanol and others.

The compounds of the invention or mixtures are preferably used in the form of compositions such as powders, dusting agents, granulates, solutions, emulsions or suspensions, together with liquid and/or solid carrier materials or diluents and, if desired, also cross-linking, adhesion improving, emulsifying and/or dispersion agents.

Suitable liquid carrier materials are, for instance, water, aliphatic and aromatic hydrocarbons such as benzene, toluene, xylene, cyclohexanone, isophorone, dimethylsulfoxide, dimethylformamide, and furthermore mineral oil fractions.

As solid carrier materials there may be used mineral earths, for instance, tonsil, silicagel, talcum, kaolin, attaclay, limestone, silicic acid, and plant products such as flours.

Surface active agents which may be used in the compositions of the invention are, for instance, calcium-lignosulfonate, polyoxyethylene-alkylphenylether, naphthalene sulfonic acid and their salts, phenolsulfonic acids and their salts, formaldehyde condensation products, fatty alcohol sulfates, as well as substituted benzosulfonic acids and their salts.

The amount of the active agents in the different compositions can be varied widely. For instance, the composition may contain between 10 and 80% by weight of active agents, between about 90 and 20% by weight of liquid or solid carrier materials and, if desired, up to 20% by weight of surface active agents.

The application of the compounds or compositions can be effected in conventional manner. For instance, it may be carried out with water as carrier materials in spray amounts of about 100 to 1000 liter to about 2.5 acres. It is possible to use the compounds in the so-called low volume processes and ultra low volume processes as well as in form of so-called micro granulates.

Preferred among the compounds of the invention are particularly those in which in the above general formula $R_1$ is hydrogen or alkyl of 1 to 5 carbon atoms, $R_2$ is hydrogen or alkyl of 1 to 5 carbon atoms, and $R_3$ is a pyridyl or pyrimidyl residue which may also be substituted by one or more of the same or different substituents composed of alkyl of 1 to 4 carbon atoms, alkoxy of 1 to 4 carbon atoms, halogen, nitro or trifluoromethyl.

As alkyl residues for use in the above compositions may be mentioned methyl, ethyl, propyl, n-butyl and n-pentyl.

As substituents for the heterocyclic hydrocarbon residue which includes at least one nitrogen atom in the ring and which may preferably be a pyridyl or pyrimidyl residue there may be mentioned the following: methyl, ethyl, propyl, n-butyl, methoxy, ethoxy, propoxy, chlorine, bromine, the nitro- and the trifluoromethyl groups.

PROCESS OF MAKING

The compounds of the invention can be made in different ways.

A. One way of making the compounds is to react a compound of the formula

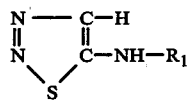

with a chloroformic acid ester of the formula

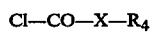

in the presence of an acid acceptor such as triethylamine, N,N-dimethylaniline, hexamethyl phosphoric acid triamide or a pyridine base, in an organic solvent as for instance tetrahydrofuran, methylene chloride and dimethylformamide at a temperature between 0° and 60° C. and preferably at room temperature. The product obtained is then reacted with an amine of the formula

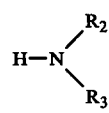

in an organic solvent for instance acetone, dimethylformamide, tetrahydrofuran and acetonitrile at a temperature between 50° and 150° C. Preferably, the reaction is at the boiling point of the solvent.

$R_1$, $R_2$ and $R_3$ in these formulas have the same meaning as above, while X is oxygen or sulfur, and $R_4$ is alkyl of 1 to 5 carbons or aryl, for instance phenyl.

B. Another form of making the compounds of the invention is to react the compound of the formula

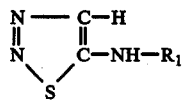

with phosgene in the presence of an acid acceptor for instance N,N-dimethylaniline so as to form the corresponding isocyanate or carbamoylchloride. The product of this reaction is then again reacted with an amine of the formula

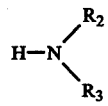

The reaction products are then isolated in conventional manner. $R_1$, $R_2$ and $R_3$ in the reaction group B have the same meaning as before.

The following Examples will further illustrate the making of the compounds of the invention.

EXAMPLE 1

1-(2-pyridyl)-3-(1,2,3-thiadiazole-5-yl)-urea 16.5 g (0.075 mol) 5-phenoxycarbonylamino-1,2,3-thiadiazole are suspended in 150 ml acetone and reacted with 9.4 g (0.1 mol) of 2-aminopyridine. The reaction mass is then refluxed for 3 hours. After cooling to room temperature the formed light brown crystals are removed by suction and dried. They are then recrystallized from ethanol. There is thus obtained the above noted title compound (compound No. 1).

Yield: 9.3 g = 56.3% of the theoretical value, colorless crystals having an m.p. of 227° C. (upon decomposition).

Analysis: theoretical C 43.41%, H 3.19%, N 31.67%, S 14.50%. obtained 43.86%, 3.24%, 31.89%, 14.20%.

The starting product for making the above compound No. 1 is 5-phenoxycarbonylamino-1,2,3-thiadiazole. This is made as follows:

A solution of 10.1 g (0.1 mol) 5-amino-1,2,3-thiadiazole in 75 ml tetrahydrofuran is reacted with 17.4 ml (0.1 mol) hexamethylphosphoric acid triamide. There are then added dropwise 15.7 g (0.1 mol) of chloroformic acid phenylester until the temperature reaches a maximum of 60° C. After stirring for 5 hours at room temperature the mixture is then diluted with 400 ml water. The crystals are removed by suction, dried and recrystallized from ethanol.

Yield: 19.5 g = 88.1% of the theoretical value m.p.: 218°-220° C. (upon decomposition).

In an analogous manner, the following compounds have been made:

| Ex. No. | Compound | Physical constants |
|---|---|---|
| 2 | 1-(5-chloro-2-pyridyl)-3-(1,2,3-thiadiazole-5-yl)-urea | m.p.: 255° C (decomposed) |
| 3 | 1-(4-methyl-2-pyridyl)-3-(1,2,3-thiadiazole-5-yl)-urea | m.p.: 233° C (decomposed) |
| 4 | 1-(4-methyl-2-pyrimidyl)-3-(1,2,3-thiadiazole-5-yl-urea | m.p.: 235° C (decomposed) |
| 5 | 1-(4-pyridyl)-3-(1,2,3-thiadiazole-5-yl)-urea | m.p.: 215° C (decomposed) |
| 6 | 1-(3-pyridyl)-3-(1,2,3-thiadiazole-5-yl)-urea | m.p.: 218° C (decomposed) |
| 7 | 1-(2-pyrimidyl)-3-(1,2,3-thiadiazole-5-yl)-urea | m.p.: >270° C (decomposed) |
| 8 | 1-(3-methyl-2-pyridyl)-3-(1,2,3-thiadiazole-5-yl)-urea | m.p.: 234° C (decomposed) |
| 9 | 1-(5-methyl-2-pyridyl)-3-(1,2,3-thiadiazole-5-yl)-urea | m.p.: 230° C (decomposed) |
| 10 | 1-(6-methyl-2-pyridyl)-3-(1,2,3-thiadiazole-5-yl)-urea | m.p.: 234° C (decomposed) |

The compounds of the invention are color and odorless crystalline substances which are not soluble in water or aliphatic or aromatic hydrocarbons. They have a better solubility in polar organic solvents such as acetone, isophorone, cyclohexanone, dimethylsulfoxide and dimethylformamide.

The following test results further illustrates the uses of the compounds of the invention:

EXAMPLE 11

In a hothouse potted bushbeans (*Phaseolus vulgaris*), after formation of the primary leaves, and soybeans (*Glycine maxima*), at initial development of the first trifoliate were treated with different amounts as indicated of the compound of the invention listed below. The active agent was set up as a 20% concentration spray powder and was applied in an aqueous suspension in a total liquid amount of 500 liters of spray liquid per about 2.5 acres. The growth regulating effect was determined 2 weeks after treatment by measuring the length of the first internodule. The measurements were then related to the untreated controls and calculated as the percentage growth retardation.

As appears from the table a growth regulating effect was obtained in a broad range of concentrations without any burn damage to the leaves:

| Compound | Amount of active agent kg/2.5 acres | Retardation in % bushbeans | soybeans |
|---|---|---|---|
| 1-(2-pyridyl)-3-(1,2,3-thiadiazole-5-yl)urea | 0.1 | 33 | 30 |
|  | 0.3 | 47 | 40 |
|  | 1.0 | 60 | 55 |
|  | 3.0 | 65 | 60 |
| Untreated | — | 0 | 0 |

EXAMPLE 12

Growing cotton plants at the stage of 8 to 10 developed foliage leaves were treated with 0.5 kg effective agent per about 2.5 acres. The agent was as indicated below. The amount of water employed for the suspension was 500 liters per about 2.5 acres.

| Compound | Amount of active agent kg/2.5 acres | % Defoliation after 6 days |
|---|---|---|
| 1-(2-pyridyl)-3-(1,2,3-thiadiazole-5-yl)-urea | 0.5 | 50.0 |
| Control tri-n-butyl-trithiophosphate | 0.5 | 25.8 |

| Compound | Amount of active agent kg/2.5 acres | % Defoliation after 6 days |
|---|---|---|
| Untreated | — | 0 |

As the Table shows the compound of the invention is definitely superior regarding intensity of activity and speed of activity.

In the above statements regarding area treated the calculation was initially made in regard to hectares. For convenience 1 hectare was figured as about 2.5 acres in the Anglo Saxon system.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A 1,2,3-thiadiazole-5-yl-urea derivative of the formula

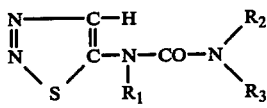

in which $R_1$ is hydrogen or alkyl of 1 to 5 carbon atoms;
$R_2$ is hydrogen or alkyl of 1 to 5 carbon atoms;
$R_3$ is a pyridine residue which residue may also be substituted by one or more of the same or different substituents, the substituents being selected from the group consisting of alkyl of 1 to 4 carbon atoms, alkoxy of 1 to 4 carbon atoms, halogen, nitro- and trifluoromethyl.

2. The compound of claim 1 which is 1-(2-pyridyl)-3-(1,2,3-thiadiazole-5-yl)-urea.
3. The compound of claim 1 which is 1-(5-chloro-2-pyridyl)-3-(1,2,3-thiadiazole-5-yl)-urea.
4. The compound of claim 1 which is 1-(4-methyl-2-pyridyl)-3-(1,2,3-thiadiazole-5-yl)-urea.
5. The compound of claim 1 which is 1-(4-pyridyl)-3-(1,2,3-thiadiazole-5-yl)-urea.
6. The compound of claim 1 which is 1-(3-pyridyl)-3-(1,2,3-thiadiazole-5-yl)-urea.
7. The compound of claim 1 which is 1-(3-methyl-2-pyridyl)-3-(1,2,3-thiadiazole-5-yl)-urea.
8. The compound of claim 1 which is 1-(5-methyl-2-pyridyl)-3-(1,2,3-thiadiazole-5-yl)-urea.
9. The compound of claim 1 which is 1-(6-methyl-2-pyridyl)-3-(1,2,3-thiadiazole-5-yl)-urea.
10. A composition for obtaining plant growth retardation and defoliation, the said composition comprising about 10 to 80% of at least one compound of claim 1 and about 90 to 20% of a liquid or solid carrier material.
11. The composition of claim 10 which includes about 20% of a surface active agent.
12. A method of causing growth retardation and defoliation in plants comprising applying to the plant or to the ground in which the plant is grown the composition of claim 10 in an amount of about 0.05 to 5 kg per about 2.5 acres of ground.

* * * * *